US007645425B2

(12) United States Patent
Haywood et al.

(10) Patent No.: US 7,645,425 B2
(45) Date of Patent: *Jan. 12, 2010

(54) PROTEASE INHIBITOR SAMPLE COLLECTION SYSTEM

(75) Inventors: Bruce Haywood, Franklin Lakes, NJ (US); Ajit Dastane, Bridgewater, NJ (US); Fu-Chung Lin, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/937,954

(22) Filed: Nov. 9, 2007

(65) Prior Publication Data

US 2008/0241001 A1   Oct. 2, 2008

Related U.S. Application Data

(63) Continuation of application No. 10/436,263, filed on May 13, 2003, now Pat. No. 7,309,468.

(60) Provisional application No. 60/379,399, filed on May 13, 2002.

(51) Int. Cl.
*B01L 3/00* (2006.01)
(52) U.S. Cl. ............... 422/102; 422/99; 422/101; 436/63; 436/176; 435/2
(58) Field of Classification Search ............... 422/99, 422/100, 101, 102, 61; 436/18, 63, 174, 436/176, 177; 435/2
See application file for complete search history.

(56) References Cited

U.S. PATENT DOCUMENTS 3,929,646 A   12/1975   Adler
3,995,630 A   12/1976   van de Veerdonk et al.
4,153,739 A   5/1979    Kessler
4,154,690 A   5/1979    Ballies et al.
4,190,535 A   2/1980    Luderer et al.
4,257,886 A   3/1981    Kessler
4,350,593 A   9/1982    Kessler
4,417,981 A   11/1983   Nugent (Continued)

FOREIGN PATENT DOCUMENTS

DE   2629808   1/1978

(Continued)

OTHER PUBLICATIONS

Haematologic Technologies, Inc. brochure, 2002-2003 Research Reagents Catalog, pp. E-13 to E-14.*

(Continued)

*Primary Examiner*—Maureen M Wallenhorst
(74) *Attorney, Agent, or Firm*—Lerner, David, Littenberg, Krumholz & Mentlik, LLP

(57) ABSTRACT

A collection container and a method for collecting a biological sample, particularly whole blood, includes at least one stabilizing agent in an amount effective to stabilize and inhibit protein degradation and/or fragmentation. The stabilizing agent is able to stabilize proteases in the biological sample, particularly at the point of collection, by inhibiting protein degradation and/or fragmentation in the sample when the sample is stored. The stabilizing agent includes one or more protease inhibitors.

26 Claims, 8 Drawing Sheets

U.S. PATENT DOCUMENTS

| | | |
|---|---|---|
| 4,677,075 A | 6/1987 | Louderback et al. |
| 4,703,013 A | 10/1987 | Louderback et al. |
| 4,737,152 A | 4/1988 | Alchas |
| 4,751,001 A | 6/1988 | Saunders |
| 4,818,418 A | 4/1989 | Saunders |
| 4,917,801 A | 4/1990 | Luderer et al. |
| 4,919,889 A | 4/1990 | Jones et al. |
| 4,964,886 A | 10/1990 | Brugerolle et al. |
| 4,986,818 A | 1/1991 | Imbert et al. |
| 5,030,215 A | 7/1991 | Morse et al. |
| 5,030,341 A | 7/1991 | McEwen et al. |
| 5,053,134 A | 10/1991 | Luderer et al. |
| 5,096,811 A | 3/1992 | Hotchkiss et al. |
| 5,171,669 A | 12/1992 | Burdick et al. |
| 5,198,365 A | 3/1993 | Grow et al. |
| 5,240,843 A | 8/1993 | Gibson et al. |
| 5,354,483 A | 10/1994 | Furse et al. |
| 5,378,601 A | 1/1995 | Gepner-Puszkin |
| 5,486,459 A | 1/1996 | Burnham et al. |
| 5,541,116 A | 7/1996 | Bergmann et al. |
| 5,543,048 A | 8/1996 | Vogler et al. |
| 5,585,273 A | 12/1996 | Lawrence et al. |
| 5,607,400 A | 3/1997 | Thibault et al. |
| 5,627,029 A | 5/1997 | Houseal et al. |
| 5,667,963 A | 9/1997 | Smith et al. |
| 5,670,558 A | 9/1997 | Onishi et al. |
| 5,681,743 A | 10/1997 | Brian et al. |
| 5,721,139 A | 2/1998 | Mather et al. |
| 5,728,581 A | 3/1998 | Schwartz et al. |
| 5,786,227 A | 7/1998 | Charlton |
| 5,788,862 A | 8/1998 | Degen et al. |
| 5,801,055 A | 9/1998 | Henderson |
| 5,853,894 A | 12/1998 | Brown |
| 5,860,937 A | 1/1999 | Cohen |
| 5,882,922 A | 3/1999 | Tyndorf et al. |
| 5,906,744 A | 5/1999 | Carroll et al. |
| 5,932,473 A | 8/1999 | Swiderek et al. |
| 5,945,457 A | 8/1999 | Plate et al. |
| RE36,331 E | 10/1999 | Arduini et al. |
| 5,995,371 A | 11/1999 | Suzaki |
| 5,998,216 A * | 12/1999 | O'Donnell ............... 436/176 |
| 6,027,481 A * | 2/2000 | Barrelle et al. ............. 604/187 |
| 6,077,523 A | 6/2000 | Deghenghi et al. |
| 6,117,650 A | 9/2000 | King |
| 6,127,340 A | 10/2000 | Green et al. |
| 6,184,210 B1 | 2/2001 | Keana et al. |
| 6,197,325 B1 | 3/2001 | MacPhee et al. |
| 6,225,123 B1 | 5/2001 | Cohen et al. |
| 6,263,641 B1 | 7/2001 | Odell et al. |
| 6,280,689 B1 * | 8/2001 | Stevens ................... 422/100 |
| 6,309,885 B1 | 10/2001 | Probst et al. |
| 6,328,726 B1 | 12/2001 | Ishida et al. |
| 6,343,717 B1 | 2/2002 | Zhang et al. |
| 6,357,583 B1 | 3/2002 | Rainen |
| 6,406,671 B1 | 6/2002 | DiCesare et al. |
| 6,409,528 B1 * | 6/2002 | Bodnar ..................... 439/177 |
| 6,440,934 B1 | 8/2002 | Whitehouse |
| 6,497,325 B1 | 12/2002 | DiCesare et al. |
| 6,506,167 B1 | 1/2003 | Ishimito et al. |
| 6,516,953 B1 | 2/2003 | DiCesare et al. |
| 6,617,170 B2 | 9/2003 | Augello et al. |
| 6,835,814 B1 | 12/2004 | Micanovic et al. |
| 7,309,468 B2 * | 12/2007 | Stevens et al. ............ 422/102 |
| 2002/0146677 A1 | 10/2002 | Augello et al. |
| 2003/0013205 A1 * | 1/2003 | Konrad ..................... 436/177 |
| 2004/0013575 A1 | 1/2004 | Stevens et al. |
| 2004/0038424 A1 | 2/2004 | Maples |
| 2004/0067889 A1 | 4/2004 | Belenky et al. |
| 2004/0175754 A1 | 9/2004 | Bar-Or et al. |
| 2006/0212020 A1 | 9/2006 | Rainen et al. |

FOREIGN PATENT DOCUMENTS

| | | |
|---|---|---|
| EP | 0100673 | 2/1984 |
| EP | 0 431 385 | 6/1991 |
| EP | 0542255 | 5/1993 |
| JP | 3295465 | 12/1991 |
| JP | 03297392 | 12/1991 |
| JP | 04-249767 | 9/1992 |
| JP | 5249104 | 9/1993 |
| JP | 6273418 | 9/1994 |
| WO | 9307489 | 4/1993 |
| WO | 03018757 | 3/2003 |

OTHER PUBLICATIONS

SYDPATH The Institute of Laboratory Medicine, http:/www.sydpath.stvincents.com.au/tests/PTHrP.htm.

Haematologic Technologies, Inc., '2002' Research Reagents Catatog, pp. E-13 to E.14.

SIGMA Product Information, "Protease Inhibitor Cocktail", Product No. P2714.

Weissman, M., and Klein B., Evaluation of glucose determinations in untreated serum samples. Clinical Chemistry, (1958), 420-422,4.

NH. Wallen et al. (1997). "influence of different anticoagulants on platelet aggregation in whole blood: a comparison between citrate, low molecular mass heparin and hirudin" 87, pp. 151-157.

S.C. Sansom et al. (1997). "Regulation of large calcium-activated potassium channels by protein phosphatase 2a" 272. pp. 9902-9906.

Chuang, et al. (1998). "Effects of anticoagulants in amino acid analysis: comparisons of heparin, EDIA. and sodium citrate in vacutainer tubes for plasma preparation," Clinical Chemistry vol. 44, No. 5, pp. 1052-1056.

KM. Eyster et al. (1998). Protein phosphatase activity in the rat ovary throughout pregnancy and pseudopregnancy, "Biology of Reproduction" 58, pp. 338-345.

BD Vacutainer Venous Blood Collection Tube Guide, published circa Jan. 2005.

Brain L. Hood; Thomas P. Conrads and Timothy D. Veenstra, Mass Spectrometric analysis of formalin•fixed paraffin-embedded tissue: Unlocking the proteome within, Proteomics 2006, 4106-4114, 6, Wiley-VCH Verlag GmbH & Co. KGaA, Weinheim.

Jeremy E. Melanson, Steven L. Avery and Devanand M. Pinto, High-coverage quantitative proteomics using amine-specific isotopic labeling, Proteomics 2006,4466-4474,6, Wiley-VCH Verlag GmbH & Co. KGaA, Weinheim.

Joerg Reinders and Albert Sickmann, State-of-the-art in phosphoproteomics, Proteomics 2005, 4052-4061,5, Wiley•VCH Verlag GmbH & Co. KGaA, Weinheim.

Harry Eagle, Stanley Barban, Mina Lew, and Henry O. Schulze "The Utilization of Carbohydrates by Human Cell Cultures", Carbohydrate Utilization by Cell Cultures 1958. vol. 233, No. 3, p. 551.

Sabine Wilhelm, Sandra Roloff. Geory Haecker "Inhibition of etoposide-induced apoptotic events by azide" Immunology Letters 59(1997)53-59.

H. Shimizu et al., Clinica Chimica Acta, Mar. 2001, 305: 181-186.

H. Shimizu et at., Clinica Chimica Acta, Jul. 1999, 285: 169-172.

A.Goginet-Georges et al., Clin. Chem. Lab. Med., 2000, 38(6): 519-523.

E. Morita et al., Circulation, 1993, 88:82-91.

T. Tsutamoto et al., Am. Heart J., 1989, 117: 599-606.

M. Mukoyama et al., Lancet, 1990, 335: 801-802.

T.A. McDonagh et al.. Lancet, 1998,351:9-13.

T. Omland et al.. Circulation, 1996,93: 1963-1969.

T. Tsutamoto et at., Circulation, 1997,96:509-516.

D.R. Murdoch et at., Heart, 1999. 81 212-213.

T. Tsuju et al., Clin. Chem., 1994, 40(4): 672-673.

B. Bluestein et al., Clinical Chemistry, Jun. 14, 2002, 48(S6): A85. Abstract C37.

MaCarthy et al. , Cylometry 23 (3) 196-204, Mar. 1996.

* cited by examiner

PROTEASE INHIBITOR SAMPLE COLLECTION SYSTEM

CROSS-REFERENCE TO RELATED APPLICATIONS

The present application is a continuation of U.S. Patent application Ser. No. 10/436,263 filed May 13, 2003, now U.S. Pat. No. 7,309,468 issued on Dec. 18, 2007, which claims priority to U.S. Provisional Patent Application Ser. No. 60/379,399, which was filed on May 13, 2002.

FIELD OF THE INVENTION

The present invention is directed to a method and device for collecting and stabilizing a biological sample, particularly a whole blood sample, directly from a patient. More specifically, the present invention relates to sample collection containers having a stabilizing additive contained therein for stabilizing proteases immediately on collection of a biological sample and for inhibiting protein degradation and/or fragmentation during storage thereof.

BACKGROUND OF THE INVENTION

In clinical diagnostic settings, it has often been necessary to collect biological samples such a whole blood, red blood cell concentrates, platelet concentrates, leukocyte concentrates, tissue, bone marrow apirates, plasma, serum, cerebral spinal fluid, feces, urine, cultured cells, saliva, oral secretions, nasal secretions and the like in various containers or tubes for subsequent testing and analysis. Typically, the samples must then be transported to a different location, such as a laboratory, where personnel conduct specific tests on the samples.

Generally, a considerable amount of time elapses between obtaining the sample and analyzing it. A common and recurring problem, therefore, is the maintenance of the biological sample in a manner that prevents degradation, alteration or destruction of essential materials during the manipulations and/or preparations preceding analysis of the biological sample as a test specimen. All cells contain a number of proteases and, as long as the cells are intact, the proteases do not damage the cellular components. Once the cells are frozen, broken up or disrupted, however, protease enzymes begin to react on cellular proteins unspecifically, thereby quickly degrading the cellular proteins. In protein isolation, this can lead to degraded or fragmented proteins. This also can lead to a decline in protein levels during storage and transport of biological samples, thereby limiting the sensitivity of testing methods. The yield of the protein(s), therefore, can be drastically reduced and can endanger all further subsequent experiments such as, for example, protein quantification, 2-D gel plotting of proteins, drug development, Western blotting, reporter gene analysis, immunoprecipitations, epitope tagging, specific protein activity assays, etc.

It has long been recognized that the body fluid sample must be maintained and preserved during the manipulations and/or preparations preceding analysis as a test specimen. A number of different compositions have been developed for maintaining the stability of the cellular fraction or the non-cellular components of a test sample during the preparatory stages. These include, for example, the use of a water-soluble phosphate such as ATP and a chelating agent for the preservation of whole cells or cellular components (Publication EP 431385-A); the use of an acid, anti-bacterial drug, and fluorine compound in combination for stabilization of cells in urine (Japanese Patent Publication 05249104-A); the use of an aqueous solution of ethanol, aliphatic diol and polyethylene glycol for preserving cell or blood fluid components (Japanese Patent Publication 03295465-A); a reagent composition for biological assays that contains a reducible water-soluble trivalent cobalt complex, metallisable dye, and water-soluble polymer (U.S. Pat. No. 5,171,669); a stability control solution for determination of urobilinogen in urine samples (U.S. Pat. Nos. 4,677,075 and 4,703,013); the use of an aqueous solution containing phosphate buffer, albumin, glycine, and cysteine for stabilizing dehydrogenases (German Patent Publication DE2629808-A); a stabilizing composition comprising a buffer, alanine and mannitol for stabilization of freeze-dried protein compositions (Publication EP682944-A1); and the use of cationic poly-electrolyte and cyclic polyiol in aqueous solutions to stabilize proteins against denaturation on drying (U.S. Pat. No. 5,240,843). A number of stabilizing preparations have been commercially manufactured and sold, a notable example being the COMPLETE® protease inhibitor cocktail tablets for the inhibition of proteases during extractions from animal and plant tissues.

Despite the development and commercial availability of stabilizing preparations and compositions, the overwhelming majority of these are quite limited as to their usefulness and efficacy and do not lend themselves without major modification and alterations to specific clinical problems or a broad variety of different clinical and analytical settings. For example, many such compositions do not stabilize the proteases in the sample, thereby failing to preserve sensitive proteins in the biological samples.

In the area of blood collection, a common additive generally used in blood samples prior to centrifuging to separate the blood into cell layers is an anticoagulation additive. Typically, the anticoagulation additive is a buffered citrate or heparin in an aqueous solution. Blood collection tubes containing an anticoagulant are commercially manufactured and sold. An example of such a tube is disclosed in U.S. Pat. No. 5,667,963 to Smith et al.

Attempts have also been made to prevent the degradation of peptides by adding EDTA and/or proteolysis inhibitors to the sample. For example, U.S. Pat. No. 5,541,116 discloses the use of two protease inhibitors, anastatin and leupeptin, in combination with EDTA for stabilizing peptides in whole blood, serum or plasma samples. The patent, however, discloses stabilizing the samples by adding an adequate amount of the stabilizing combination to the samples themselves after they have been obtained or after thawing in situations where the sample had previously been frozen after collection thereof.

Additionally, it is known that in some laboratories studying proteomics, protease inhibitor cocktails are manually drawn into syringes and then injected into blood collection tubes. This procedure, however, is dangerous because of the likelihood of needle stick injuries. Moreover, the volumes of the protease inhibitor cocktails are subject to technician-to-technician variability because of the manual method of loading the protease inhibitor cocktails into the tubes.

The issue of industry standardization for a protease cocktail, i.e. a combination of protease inhibitors, is also significant. First of all, different companies and different researchers are introducing a spectrum of protease inhibitors to collected samples, particularly blood or a component thereof. The effectiveness and behavioral differences of the protease inhibitors and combinations thereof are, ostensibly, not well studied and, therefore, it is extremely difficult to correlate one researcher's analytical results to another researcher's results. For example, a 2-D gel could present a certain set of information for blood that has been introduced to a protease inhibitor cocktail supplied by Sigma-Aldrich Company and yet present a different set of information for blood introduced to a protease inhibitor cocktail supplied by Becton, Dickinson and Company or by Hoffmann-La Roche, Inc. In addition, most protease inhibitors range in toxicity from mildly toxic to highly toxic. Presently, there is no control and/or limit to potential exposure to these toxins, thereby jeopardizing the safety of healthcare and laboratory workers.

Measures must be taken to inhibit endogenous protease for the isolation and purification of proteins. Measures must also be taken leading to industry standardization. Accordingly, there is a continuing need in the industry for an improved method and a collection device for blood and other biological samples that preserve the proteins present in the biological samples.

SUMMARY OF THE INVENTION

Surprisingly, it has now been found that collecting a biological sample from a patient and introducing that sample into a container containing a stabilizing agent can be efficient in maintaining protein content and composition. Inclusion of the stabilizing agent within the collection device for immediate contact with the biological sample substantially prevents the degradation and/or fragmentation of proteins that otherwise occurs between the time the sample is collected and the stabilizing agent is added. As a result, the percentage of intact proteins is greatly increased.

The present invention, therefore, is directed to methods and devices for collecting a biological sample. More particularly, the invention is directed to a collection container and to a method of collecting a biological sample, which comprises immediately contacting the sample with a stabilizing additive to inhibit endogenous protease for the isolation and purification of proteins. The stabilizing agent of the invention is a suitable agent that is able to inhibit, prevent or reduce the occurrence of protein degradation and/or fragmentation during storage of the biological sample.

Accordingly, a primary aspect of the present invention is to provide a method and device for collecting a biological sample directly from a patient in the presence of a stabilizer capable of inhibiting endogenous protease for the isolation and purification of proteins. The stabilizing additive is present in an effective amount to stabilize the biological sample and to inhibit endogenous protease for the isolation and purification of proteins. Desirably, the sample is whole blood or a component thereof; however, the sample may be any protein-containing sample.

One aspect of the present invention is to prepare a biological sample that is stable at room temperature for extended periods of time with little or no degradation or fragmentation of proteins. Accordingly, a method is provided for producing a biological sample that is stable at room temperature for extended periods of time with little or no incidence of degradation or fragmentation of proteins during storage.

A further aspect of the invention is to provide a method and device for inhibiting degradation or fragmentation of proteins in a biological sample.

Another aspect of the invention is to provide a collection container for receiving and collecting a biological sample where the container is pre-sealed with a measured quantity of a stabilizing agent. The stabilizing agent may be supplied in the form of, for example, a liquid, a liquid or solid aerosol, a pellet, a powder or a gel to any surface of the container.

A further aspect of the present invention is to provide a method for stabilizing a biological sample, particularly whole blood or a component thereof, immediately upon collection from the patient to inhibit or prevent degradation or fragmentation of proteins when the sample is stored at various temperatures.

Another aspect of the present invention is to provide an evacuated container that is supplied with an effective amount of a stabilizing agent, where the container has an internal pressure sufficiently low to draw a predetermined volume of a biological sample into the container.

Still another aspect of the present invention is to provide a blood collection container for collecting an amount of blood and mixing the blood with a stabilizing agent at the point of collection to produce a blood sample that is stable by preventing degradation or fragmentation of proteins such that isolation and purification of proteins in the sample can be conducted at a later time.

The aspects of the invention are basically attained by providing an apparatus for collecting a biological sample. The apparatus generally includes a container comprising at least one interior wall that defines a reservoir portion for containing a volume of a biological sample and at least one opening in communication with the reservoir portion. The container includes at least one stabilizing agent in an effective amount to preserve the biological sample and prevent or inhibit degradation or fragmentation of proteins. Preferably, the container is pre-treated with the stabilizing agent prior to collection of the sample.

The aspects of the invention are further attained by providing a method of preparing a stable biological sample, which includes providing a sample collection container. Desirably, the container has at least one side wall and a bottom defining an internal chamber where the internal chamber of the container includes at least one stabilizing agent in an amount sufficient to prevent or inhibit degradation or fragmentation of proteins and preserve a biological sample. A biological sample is obtained, and the biological sample is mixed with the stabilizing agent to form a stabilized biological sample. In one embodiment, the sample is directly introduced into the container that includes the at least one stabilizing agent.

The aspects of the invention are also attained by providing a method of collecting and stabilizing a whole blood sample, which comprises providing a sample collection container having at least one side wall and a bottom defining an internal chamber. The container is provided with an effective amount of a stabilizing agent to stabilize proteins in the whole blood sample. The internal chamber has a pressure that is preferably less than atmospheric pressure. A whole blood sample is collected directly from a patient in the collection container, and the blood sample is mixed with the stabilizing agent to form a stable whole blood sample. As the biological sample is drawn into the collection device, it is immediately exposed to the stabilizing agent, and the process of protecting protein analytes begins immediately upon introduction of the sample.

The methods and collection devices of the present invention have several distinct advantages. One advantage of the collection devices is the offering of a system, preferably a closed system, that includes the stabilizing agent and that protects the sample from deleterious exposures. Another advantage is labor relief from manual fabrication of such collection systems. Still another advantage is routine line production of such collection devices, whereby quality control measures and procedures are applied to the product. Yet another advantage is the standardization of such collection devices where no industry standards currently exist and where the industry is calling for such standardization. Moreover, the relevance of protein research and analysis is increased by preserving and being able to characterize and study proteins in a state that is as close to the in vivo state as possible.

These aspects, advantages and other salient features of the present invention will become more apparent from the following detailed description of the invention, particularly when considered in conjunction with the drawings.

BRIEF DESCRIPTION OF THE DRAWINGS

FIG. 3a is a perspective view of a sample collection assembly, while

FIG. 6a is a side view of a catheter assembly, while

DETAILED DESCRIPTION OF THE INVENTION

Figure 1:
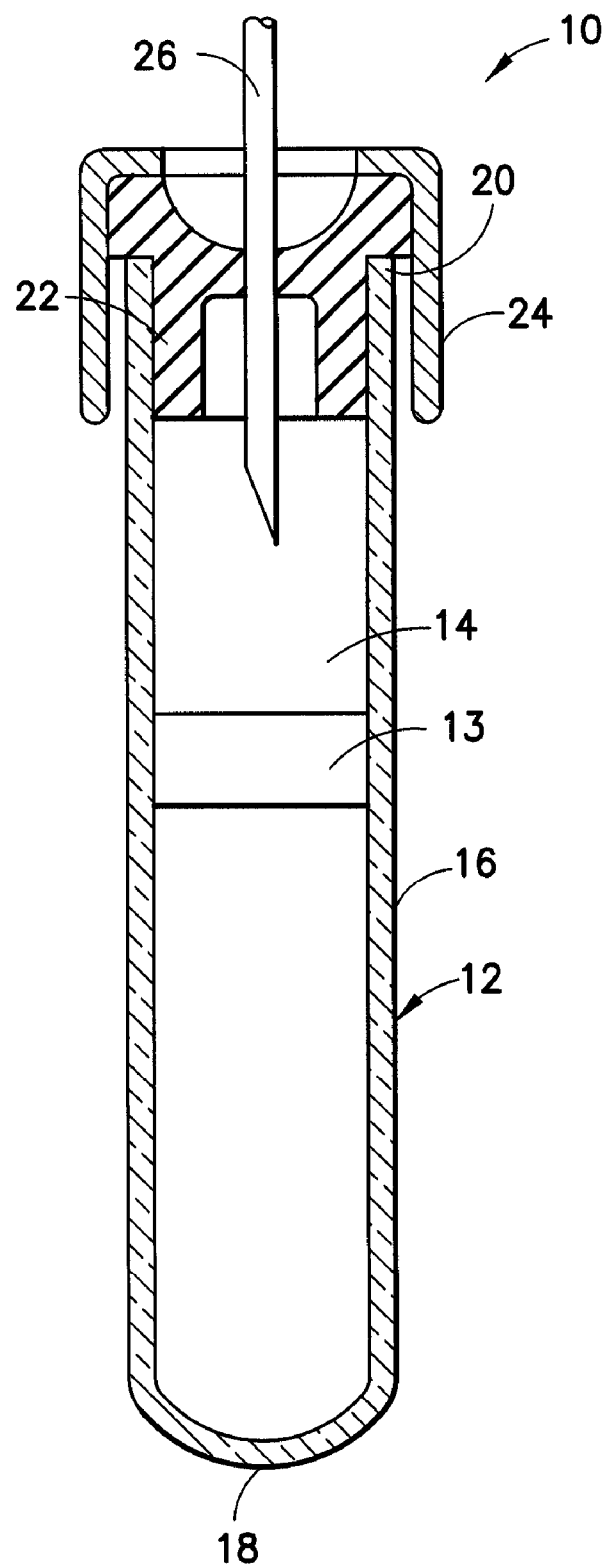
FIG. 1 is a perspective view of a typical blood collection tube.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention. The scope of the invention will be measured by the appended claims and their equivalents.

The present invention is directed to methods and devices for stabilizing a biological sample to better enable isolation and purification of proteins. More particularly, the present invention is directed to methods and devices for inhibiting protein degradation and/or fragmentation in a biological sample during storage. According to the present invention, the device comprises a container containing an amount of a stabilizing agent for admixing with a biological sample immediately on collection of the sample. Also according to the present invention, the method comprises providing a sample collection container containing a stabilizing agent in an amount sufficient to prevent or inhibit degradation and/or fragmentation of proteins and adding to the container a biological sample.

Although it is possible to use the present invention with any protein-containing biological sample, preferably the biological sample is any body fluid withdrawn from a patient. Most preferably, the biological sample is whole blood or a component thereof. Examples of other biological samples include cell-containing compositions such as red blood cell concentrates, platelet concentrates, leukocyte concentrates, plasma, serum, urine, bone marrow apirates, cerebral spinal fluid, tissue, cells, feces, saliva and oral secretions, nasal secretions, lymphatic fluid and the like.

The sample collection system of the present invention can encompass any collection device including, but not limited to, tubes such as test tubes and centrifuge tubes; closed system blood collection devices, such as collection bags; syringes, especially pre-filled syringes; catheters; microtiter and other multi-well plates; arrays; tubing; laboratory vessels such as flasks, spinner flasks, roller bottles, vials, microscope slides, microscope slide assemblies, coverslips, films and porous substrates and assemblies; pipettes and pipette tips, etc.; tissue and other biological sample collection containers; and any other container suitable for holding a biological sample, as well as containers and elements involved in transferring samples. In a particularly desirable aspect of the invention, a sample collection tube having a separating member (e.g., a mechanical separating element or a gel) for separating blood components is used. In such aspect, the interior of the tube and/or the exterior of the separating member may be treated with the stabilizing agent. According to the present invention, the collection device contains a stabilizing agent for stabilizing the biological sample.

Plastic or glass is often used to manufacture the collection device used in the present invention. Some preferred materials used to manufacture the collection device include polypropylene, polyethylene, polyethyleneterephthalate, polystyrene, polycarbonate and cellulosics. More expensive plastics such as polytetrafluoroethylene and other fluorinated polymers may also be used. In addition to the materials mentioned above, examples of other suitable materials for the collection devices used in the present invention include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF and perfluoroalkoxy resins. Glass products including silica glass are also used to manufacture the collection devices. One exemplary glass product is PYREX® (available from Corning Glass, Corning, N.Y.). Ceramic collection devices can be used according to embodiments of the invention. Cellulosic products such as paper and reinforced paper containers can also be used to form collection devices according to the invention.

The stabilizing agent of the invention is a suitable agent that is able to inhibit protease (i.e., protein enzyme) activity and the destruction of proteins during storage of a biological sample. The agent stabilizes the biological sample, such as a blood sample, to produce a stable composition that inhibits or prevents degradation and/or fragmentation of proteins present in the biological sample. In accordance with one embodiment of the present invention, the collection device is pre-treated with the stabilizing agent, preferably by the manufacturer, and is packaged in a ready-to-use form. Typically, the packaged collection device is sterile and is also packaged in sterile packaging materials.

The present invention could be used by pharmaceutical companies, biotechnology companies, contract research organizations, university researchers, research hospitals and any institution and individual who is interested in studying proteins. The present invention would enable researchers to conveniently and readily protect and process protein samples for downstream analysis. The collection device according to the present invention would serve as a front-end sample collection device aiding analytical objectives including, but not limited to the following: protein banking, protein identification and characterization, protein expression, protein quantitation, protein-protein interaction, development of protein function assays, protein target finding and validation, predictive toxicology, determination of drug action, drug validation, 3-D protein structural analysis and computer modeling.

Preferably, the stabilizing agent comprises or consists of at least one protease inhibitor. Suitable examples include, but are not limited to, inhibitors of proteases such as serine proteases, cysteine proteases, aspartic proteases, metalloproteases, thiol proteases, exopeptidases and the like. Of these, serine and cysteine protease inhibitors are of particular interest, with metalloprotease inhibitors also being significant. Non-limiting examples of serine protease inhibitors include antipain, aprotinin, chymostatin, elastatinal, phenylmethylsulfonyl fluoride (PMSF), APMSF, TLCK, TPCK, leupeptin and soybean trypsin inhibitor. Inhibitors of cysteine proteases include, for example, IAA (indoleacetic acid) and E-64. Suitable examples of aspartic protease inhibitors include pepstatin and VdLPFFVdL. Non-limiting examples of inhibitors of metalloproteases include EDTA, as well as 1,10-phenanthroline and phosphoramodon. Inhibitors of exopeptidases include, for example, amastatin, bestatin, diprotin A and diprotin B. Additional suitable examples of protease inhibitors include alpha-2-macroglobulin, soybean or lima bean trypsin inhibitor, pancreatic protease inhibitor, egg white ovostatin and egg white cystatin. Combinations of protease inhibitors, commonly referred to as a "protease inhibition cocktail" by commercial suppliers of such inhibitors, may also be used as the stabilizing agent. Such "cocktails" are generally advantageous in that they provide stabilization for a range of proteins of interest; therefore, a stabilizing agent containing more than two protease inhibitors is generally desirable.

The stabilizing agent may be in any suitable form including, but not limited to, a solution, suspension or other liquid, a pellet, a tablet, a capsule, a spray-dried material, a freeze-dried material, a powder, a particle, a gel, crystals or a lyophilized material. Because the half-life of many protease inhibitors is short, the stabilizing agent is preferably introduced into the collection device in such a form so as to optimize the shelf life of the protease inhibitor. Lyophilization appears to be particularly useful in that it provides good stability and also allows subsequent sterilization, both of which are key from a standpoint of automation and standardization.

The stabilizing agent may be located on any surface of the collection device. The stabilizing agent may also be located on stoppers and seals for closing such devices or on mechanical, or other, inserts placed within such devices. Preferably, the stabilizing agent is located anywhere along at least one interior wall of the collection device or anywhere within the reservoir portion. In addition, some protease inhibitors exhibit light sensitivity. Thus, it may be desirable to protect the agent from light. For such inhibitors, use of an opaque tube, e.g., an amber-colored tube, would be advantageous. Alternatively, placing the agent into a capsule that protects it from light exposure, e.g., in powdered form, and then placing the capsule into the tube would also address this issue. Capsulating the agent may also prevent other undesirable interactions between the agent and other elements in the container. Capsule materials that dissolve upon sample collection are well known in the art.

The stabilizing agent may be applied to the collection device by any number of methods. For example, the stabilizing agent may be spray dried, loosely dispensed or lyophilized over the surface of the interior wall of the collection device. Alternatively, the stabilizing agent, such as when in gel or liquid form, for example, may be positioned in the reservoir portion of the collection device. Additional methods for providing the collection device with the stabilizing agent are also possible. Typically, to dispose the desired amount of agent into a container, one reconstitutes a solid form of the agent and then dispenses the appropriate amount of liquid into the container. The liquid may be spray dried, disposed into the bottom of the container or subsequently lyophilized.

The quantity and location of the stabilizing agent are determined by several variables, including the mode of application, the specific stabilizing agent used, the internal volume and internal pressure of the collection device, and the volume of the biological sample drawn into the container.

The concentration of the stabilizing agent is sufficient to stabilize the proteases and to prevent protein degradation. The concentration of the stabilizing agent per ml of the specimen, depending on the specific stabilizing agent used, is about 1-200 µM, 0.1-10 mM or 0.6-25 µg.

Table I provides a non-limiting list of suitable protease inhibitors and appropriate ranges for their concentration per milliliter of specimen that may be used as the stabilizing agent.

TABLE I

| Protease Inhibitor | Concentration per milliliter of specimen |
|---|---|
| AEBSF | <5 mM, preferably <1 mM |
| Amastatin | 1-10 µM |
| Antipain | 1-100 µM |
| Antithrombin III | Use at concentration equimolar with protease |
| pAPMSF | 10-100 µM |
| Aprotinin | 0.6-2 µg |
| Bestatin | 1-200 µM, preferably 1-10 µM |
| Chymostatin | 10-100 µM |
| Cystatin | Use at concentration equimolar with protease |
| 3,4-dichloroisocoumarin | 5-100 µM |
| DFP | 100 µM |
| Diprotin A | 10-50 µM |
| E-64 | 1-10 µM |
| Ebelactone A | 1-2 µg |
| Ebelactone B | 1-2 µg |
| EDTA and its salts | 0.1-10 mM, preferably 1-10 mM |
| Elastatinal | 10-100 µM |
| Leupeptin | 0.1-100 µM, preferably 10-100 µM |
| A 2-Macroglobulin | Use at concentrations equimolar with protease |
| Pepstatin | 1 µM |
| Phosphoramidon | 25 µg (8.5 µM) |
| PMSF | 0.1 to 1 mM |
| TLCK | 10-100 µM |
| TPCK | 10-100 µM |
| Trypsin inhibitor, soybean | Use at concentration equimolar with proteases |

Stabilizing agents useful in the present invention may further include the following:

TABLE II

| Class of Inhibitor | Compound |
|---|---|
| Serine | Aprotinin |
| | AEBSF-HCl |
| | Antithrombin |
| | APMSF-HCl |
| | DFP |
| | Trypsin |
| Cysteine | E-64 |
| Serine/Cysteine | Leupeptin |
| | TPCK |
| | TLCK-HCl (L-1-chloro-3-[4-tosylamido]-7-amino-2-heptanone-HCl) |
| | Antipain-HCl |
| Metalloproteases | EDTA |
| | Bestatin |
| | Phosphoramodon |
| | Amastatin-HCl |
| Aspartic/Calpain | Pepstatin |
| | N-acetyl-leu-leu-norleucinal |
| | N-acetyl-leu-leu-methioninal |

In addition to the stabilizing agent, the device of the present invention may also contain carrier media (e.g., water or alcohol), stabilizing media (e.g., polyvinylpyrollidone, trehalose mannitol, etc.) and/or one or more other additives for treating the biological sample. Suitable additives include, but are not limited to, phenol, phenol/chloroform mixtures, alcohols, aldehydes, ketones, organic acids, salts of organic acids, alkali metal salts of halides, organic chelating agents, fluorescent dyes, antibodies, binding agents, anticoagulants such as sodium citrate, heparin, potassium EDTA and the like, and any other reagent or combination of reagents normally used to treat biological samples for analysis. Other potential additives include antioxidants and reducing agents, which may help preserve protein confirmation, e.g., preserve sulfhydryl group couplings. It may also be advantageous to include a buffering agent. Preferably, the carrier and additives do not degrade proteins. Where the stabilizing agent is in tablet form, pharmaceutical tablet disintegrating materials, which are known to those skilled in the art, may be included, if desired.

The methods of the present invention include obtaining a biological sample and introducing the sample into the container containing the stabilizing agent. In preferred embodiments, the biological sample is withdrawn from the patient directly into the collection container without any intervening process steps. It has been found that collecting the biological sample directly from the patient, such as when collecting a whole blood sample, and introducing the sample directly into the container containing the stabilizing agent substantially prevents the degradation and/or fragmentation of proteins that otherwise occurs when the sample is stored before combining it with the stabilizing agent. The method of the present invention is useful both with open collection systems and with closed collection systems wherein the opening is closed by a closure means.

In a preferred embodiment, the collection device of the present invention is for drawing a whole blood sample directly from a patient for stabilizing the proteins immediately at the point of collection. The device may be an evacuated system for collecting blood. Alternatively, the device may be a partially-evacuated or a non-evacuated system for collecting blood. A suitable example of an evacuated system is a closed tube. A manual syringe draw is a suitable example of both a partially-evacuated and a non-evacuated system. Non-evacuated systems may also include automatic draw systems. Evacuated systems are particularly preferred.

Referring to the drawings in which like reference characters refer to like parts throughout the several views thereof, FIG. 1 shows a typical blood collection device 10, which includes a container 12 defining an internal chamber 14. In the embodiment illustrated, container 12 is a hollow tube having a side wall 16, a closed bottom end 18 and an open top end 20. Optionally, a separating member 13 is provided within the container chamber 14. Separating member 13 serves to assist in separating components of the sample, for example, by centrifugation. Container 12 is dimensioned for collecting a suitable volume of biological fluid, preferably blood. A closure means 22 for covering open end 20 to close container 12 is necessary where a sterile product is demanded. For conventional tubes, a screw cap is normally sufficient. For evacuated collection tubes, a tight-fitting, elastomeric plug is generally employed to contain the vacuum during the required storage periods. Preferably, closure 22 forms a seal capable of effectively closing container 12 and retaining a biological sample in chamber 14. Closure 22 may be one of a variety of forms including, but not limited to, rubber closures, HEMOGUARD® closures, metallic seals, metal-banded rubber seals and seals of different polymers and designs. A protective shield 24 may overlie closure 22. Container 12 also contains a stabilizing agent in accordance with the present invention.

Container 12 can be made of glass, plastic or other suitable materials. Preferably, container 12 is transparent. Non-limiting examples of suitable transparent thermoplastic materials for container 12 are polycarbonates, polyethylene, polypropylene and polyethyleneterephthalate. Plastic materials can be oxygen impermeable materials or may contain an oxygen impermeable or semi-permeable layer. Alternatively, container 12 can be made of a water and air permeable plastic material. The stabilizing agent may be provided to the container using any appropriate means. In one aspect, the stabilizing agent is in a liquid solution and is placed into the container. Subsequently, the solution may be lyophilized by methods that are known in the art such as, for example, freeze drying. For example, by freezing the solution and then slowly warming after freezing, while simultaneously applying a vacuum, a freeze-dried powder remains in the collection tube. An additive such as an excipient, for example, PVP or trehalose, may also be added to the stabilizing agent solution prior to freeze drying so that the resulting stabilizing agent is pelletized in the container. Vacuum drying may also be used after adding the stabilizing solution. In another aspect, the stabilizing agent is formed into a liquid or solid aerosol and sprayed onto one or more surfaces of the interior of the container.

The pressure in chamber 14 is selected to draw a predetermined volume of biological sample into chamber 14. Preferably, closure 22 is made of a resilient material that is capable of maintaining the internal pressure differential between atmospheric pressure and a pressure less than atmospheric. Closure 22 is such that it can be pierced by a needle 26 or other cannula to introduce a biological sample into container 12 as known in the art. Preferably, closure 22 is resealable. Suitable materials for closure 22 include, for example, silicone rubber, natural rubber, styrene butadiene rubber, ethylene-propylene copolymers and polychloroprene.

Suitable examples of container 12 include single-wall and multi-layer tubes. A more specific example of a suitable container 12 is disclosed in U.S. Pat. No. 5,860,937 to Cohen, which is hereby incorporated by reference in its entirety.

A useful manufacturing process for devices according to the present invention involves obtaining a collection container; adding at least one protease inhibitor to the container; lyophilizing the at least one protease inhibitor; evacuating the container; and sterilizing the container. The at least one protease inhibitor may be dispensed into the container in solution form. After adding the protease inhibitor to the collection container, a separating member may be added to the container, if desired. An example of a suitable lyophilization/evacuation process is as follows: the container is frozen at a temperature of about −40° C. at a pressure of about 760 mm for about 6 to 8 hours; the container is dried as the temperature is ramped from −40° C. to about 25° C., at a pressure of about 0.05 mm, for about 8 to 10 hours; and the container is then evacuated at a temperature of about 25° C. and a pressure of about 120 mm for about 0.1 hours. Preferably, the sterilization technique is with cobalt 60 radiation.

As noted, container 12 may also contain a gel, mechanical or other separating member (e.g., filter paper or the like). In such cases, the stabilizing agent may be spray dried and/or lyophilized on an exterior surface of the separation media. Container 12 may also be a collection device for blood plasma preparation. Such a collection device comprises, in addition to the stabilizing agent, an element for separating plasma from human or animal whole blood. The element for separating plasma from whole blood may be a separating member such as a gel formulation or a mechanical media. The gel is desirably a thixotropic polymeric gel formulation. The gel may be a homopolymer or a copolymer and may include silicone-based gels such as, for example, polysiloxanes, or organic hydrocarbon-based gels such as, for example, polyacrylics, polyesters, polyolefins, oxidized cis polybutadienes, polybutenes, blends of epoxidized soybean oil and chlorinated hydrocarbons, copolymers of diacids and propandiols, hydrogenated cyclopentadienes and copolymers of alpha-olefins with dialkylmaleates. The gel desirably isolates the plasma from the cells of the blood sample in the tube by serving as a density separation medium. An example of a suitable plasma preparation tube is disclosed in U.S. Pat. No. 5,906,744 to Carroll et al., which is hereby incorporated by reference in its entirety. In this way, stabilization can be provided both before, during and after centrifugation to separate the plasma from the blood. In the case of a gel separating material, it may be desirable to provide physical/chemical separation between the stabilizing agent and the gel, e.g., use of a capsule as discussed above. For example, if portions of the agent are incorporated into or react with the gel, the effectiveness of the agent may be reduced. For the same reasons, where a mechanical separating element is used, the element is desirably substantially inert to the stabilizing agent, and this reflects a significant advantage of such a separator. Providing a separating element in plasma tubes, versus centrifuging without a separating element, is particularly advantageous. Specifically, because cell lysing releases the proteases that degrade proteins of interest, the better the separation between the cells (i.e., the clotted blood) and the plasma, the better the stability of proteins in the plasma sample. Useful mechanical separators are found, for example, in U.S. Pat. Nos. 6,516,953; 6,406,671; 6,409,528; and 6,497,325, the contents of which are hereby incorporated by reference in their entirety.

Container 12 may also be a collection tube for centrifugally separating lymphocytes and monocytes from heavier phases of a sample of whole blood comprising, in addition to the stabilizing agent, a liquid density gradient medium and a means for preventing mixing of the liquid density gradient medium with a blood sample prior to centrifugation. An example of a suitable lymphocyte/monocyte collection tube is disclosed in U.S. Pat. No. 5,053,134 to Luderer et al., which is hereby incorporated by reference in its entirety.

Other commercially available blood collection tubes suitable for use in the present invention include the following, all of which are sold by Becton, Dickinson and Company, Franklin Lakes, N.J., with all registrations and trademarks belonging to Becton, Dickinson and Company: VACUTAINER® hematology tubes, catalog nos. 367650-1, 367661, 6405, 6385, 6564, 367653, 367665, 367658, 367669, 6450-8, 6535-37 and 367662; VACUTAINER® K$_2$EDTA tubes, catalog nos. 367841-2, 367856 and 367861; VACUTAINER® PST tubes, catalog nos. 367793-4, 6698, 6595 and 6672; VACUTAINER® CPT tubes, catalog nos. 362753 and 362760-1; VACUTAINER® SST tubes, catalog nos. 367782-89, 6509-17 and 6590-92; and VACUTAINER® ACD tubes catalog nos. 367756, 364012 and 4816.

In another embodiment, the invention provides a kit having at least two containers comprising one or more stabilizing agents. For example, the kit may comprise a primary collection tube, e.g., a plasma separating tube having a separating element therein, and a secondary tube for testing, e.g., for pouring or otherwise dispensing the collected plasma into. Both would have stabilizing agent(s) therein, to ensure that the proteins of interest remained stable throughout. Optionally, the kit could include a tube-to-tube transfer device to prevent the need for pouring or other unsafe transfer practices, in which case the secondary tube would be at a reduced pressure to draw in the plasma. One using such a kit would collect a sample in the primary tube, centrifuge, transfer the sample of interest to the secondary testing tube, and perform the testing. The secondary testing tube could be of a variety of sizes, depending on the desired testing.

In another embodiment, the container is a tube with two open ends having closures thereon. Such a tube would allow one to sample, e.g., for a plasma separating tube with a separating element therein, either the plasma sample or the clot sample.

Figure 2:
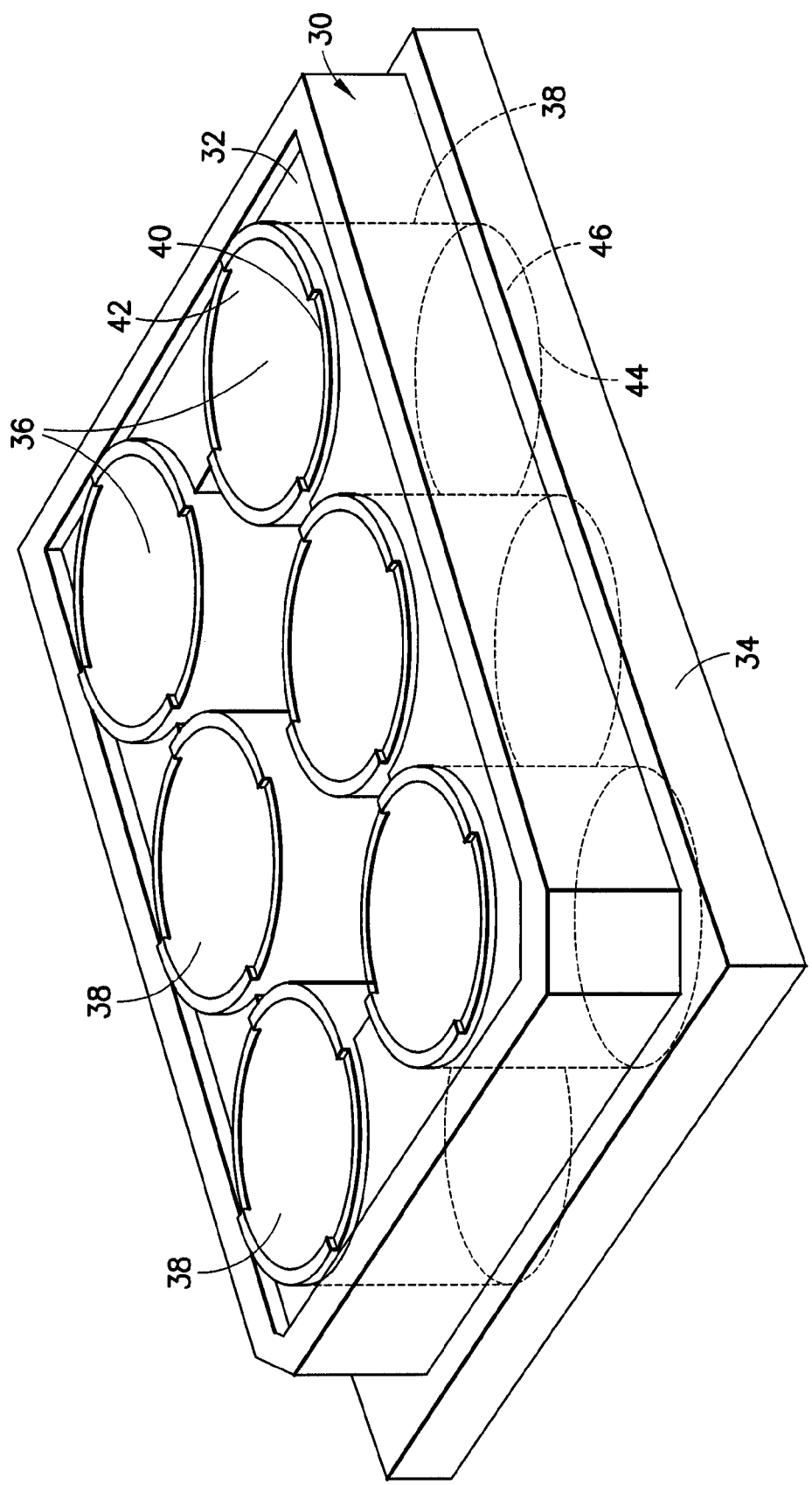
FIG. 2 is a perspective view of a test plate.

In yet another embodiment, the collection device of the present invention comprises a test plate such as, for example, a single- or multi-well plate, a microtiter plate, a tissue culture plate or the like. A typical test plate generally comprises one or more wells, which are preferably cylindrical. As shown in FIG. 2, a test plate 30 includes an upper surface 32 and a lower surface 34. Test plate 30 further includes a number of wells 36 each comprising a sidewall 38 extending from upper surface 32 of the plate to lower surface 34 of the plate. Each well comprises a top portion 40 and a bottom portion 44. Top portion 40 comprises an open end 42 that extends to bottom portion 44, which comprises a closed end 46. Bottom portion 44 may be flat, conical (pointed) or rounded. The capacity of each well 36 typically ranges from several milliliters (ml) to less than about 0.5 ml. Wells 36 may each accommodate therein a stabilizing agent according to the present invention.

The number of wells 36 in test plate 30 is not critical. There may be any number of wells, although six-, twelve-, twenty-four-, forty-eight- and ninety-six-well test plates are commonly known and available. In FIG. 2, a six-well test plate is illustrated, merely for exemplary purposes, and the invention is not dependent upon the number of wells. Most standard multi-well plates have the wells arranged in orthogonal rows and columns so as to be able to clearly identify the individual wells being used. Of course, the arrangement of the wells in test plate 30 is not an essential limitation of the present invention because any arrangement of wells is contemplated by the invention.

Plate 30 may be formed from thermoplastic materials by vacuum forming, sheet molding, injection molding or other similar techniques. Suitable thermoplastic materials include, but are not limited to, polystyrene, polyvinylchloride, polycarbonate, polyethyleneterephthalate and the like. Preferably, plate 30 is transparent.

Surrounding the wells and forming the outside border of test plate 30 are sidewalls 38. In the present embodiment, test plate 30 has six (6) sidewalls. Well known test plates are rectangle or quadrilaterally shaped, although for purposes of the present invention the plate may be fabricated in any practical configuration. Examples of suitable test plates containing a plurality of wells are disclosed in U.S. Pat. No. 5,882,922 to Tyndorf et al., U.S. Pat. No. 5,801,055 to Henderson and U.S. Pat. No. 5,681,743 to Brian et al., each of which is hereby incorporated by reference in its entirety.

In yet another embodiment, the collection device according to the present invention may be a sample collection assembly for the collection, transport and dispensing of biological samples. The collection assembly generally includes a plurality of sample wells for collecting individual biological samples. The sample wells are supported in a sample tray in a spaced-apart orientation. The sample tray may be supported within a case that encloses the sample tray and allows the safe and efficient transport of the sample wells. The sample tray is movably accommodated within the case for movement between a first position enclosing the plurality of sample wells, to a second position rendering exteriorly accessible one of the sample wells so that the sample can be manually dispensed from the tray.

Figure 3A:
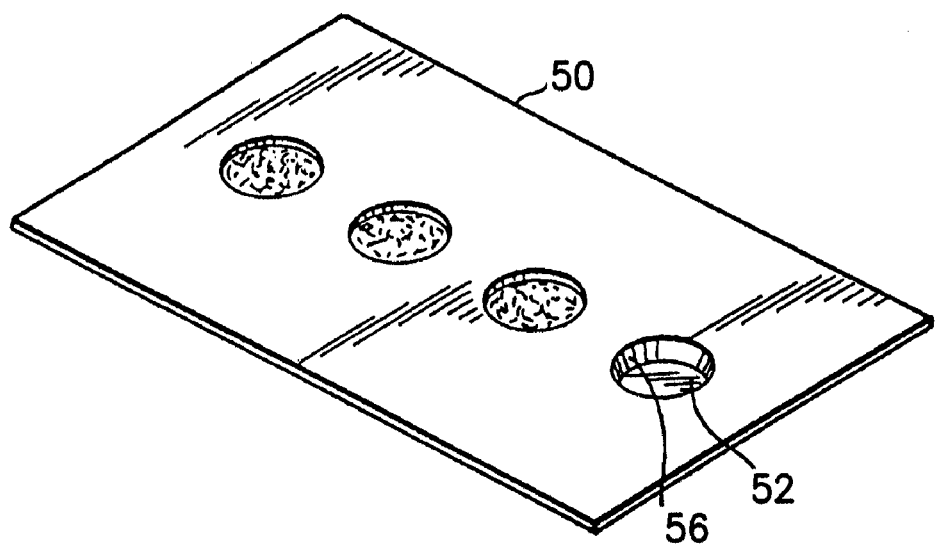
Figure 3B:
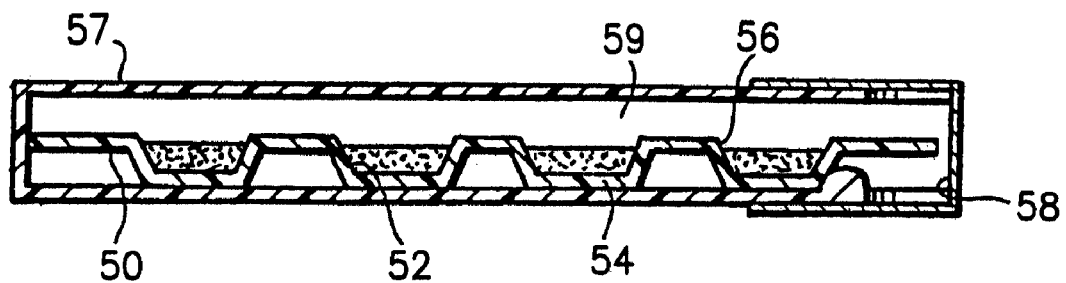
FIG. 3b is a sectional view of the sample collection assembly.

As shown in FIGS. 3a and 3b, sample tray 50 includes a plurality of longitudinally spaced depressions forming specimen collection wells 52. Sample tray 50 may be formed of a suitably deformable plastic material. Wells 52 have a bottom 54 and an open end 56. It is contemplated that the sample wells may be in the shape of open ended cup-like members. Wells 52 are constructed to have sufficient depth so as to retain a suitable volume of a biological sample. Wells 52 may each accommodate therein a stabilizing agent according to the present invention. While tray 50 of the present invention is shown having a single row of wells 52 formed therein, the present invention contemplates that the wells may be provided in any number or any array desirable for a particular testing situation. The sample collection assembly may include a sample collection case 57. Upon collection of a biological sample within wells 52, sample tray 50 may be inserted into the open end 58 of sample collection case 57 and then within the interior 59 of sample collection case 57 until all of wells 52 are enclosed therein. A suitable sample collection assembly is disclosed in U.S. Pat. No. 6,357,583 B1 to Rainen, which is hereby incorporated by reference in its entirety.

Figure 4:
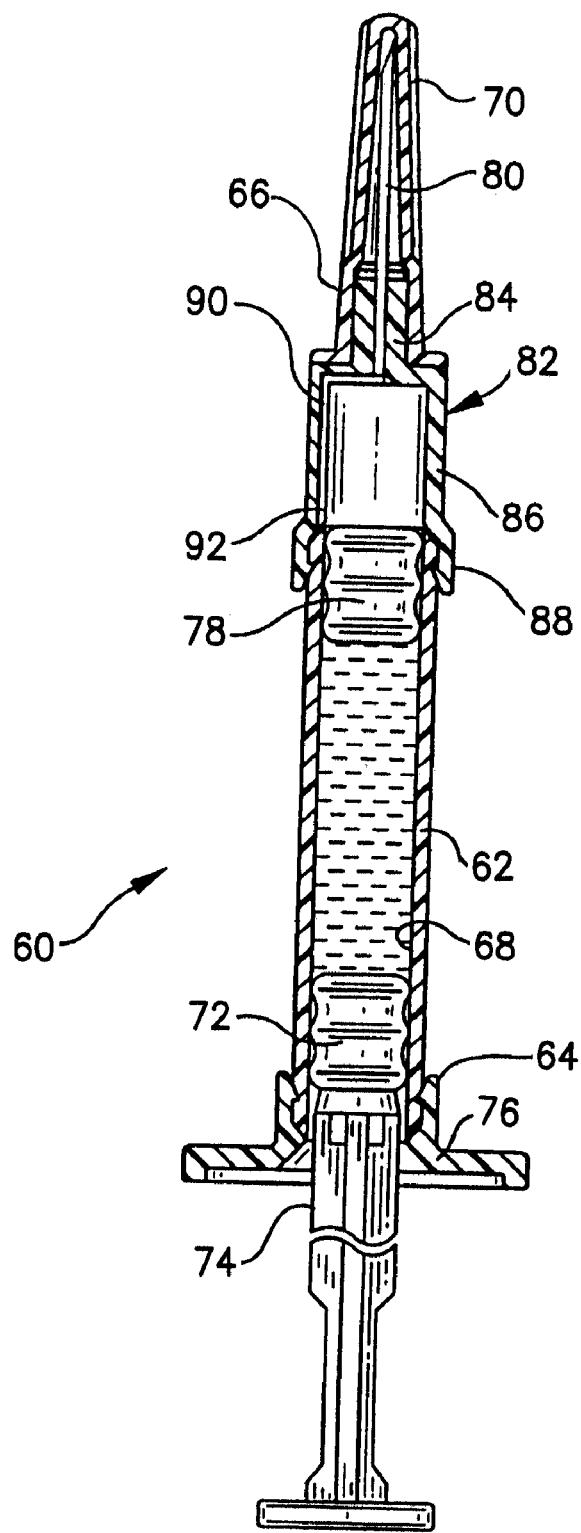
FIG. 4 is a longitudinal sectional view of a syringe.

According to another embodiment of the present invention, as depicted in FIG. 4, the collection device comprises a syringe and, more preferably, a syringe pre-filled with a stabilizing agent in accordance with the present invention. A typical syringe comprises a generally cylindrical barrel having opposed proximal and distal ends with at least one chamber formed between the ends for receiving a substance such as a biological sample. A plunger is typically sealably disposed within the barrel and movable with respect thereto, and sealing means may be sealably disposed approximate to the distal end of the barrel. Referring now to FIG. 4, there is shown a syringe 60, which includes an elongate barrel or cylinder 62 having an open, proximal end 64 and a distal end 66, with at least one hollow chamber 68 formed between the proximal and distal ends for receiving a biological sample. In the embodiment illustrated, distal end 66 includes a needle guard 70. The needle guard keeps the syringe, as well as the needle, sterile during storage.

The barrel of the syringe includes a stabilizing agent. Preferably, the barrel of the syringe is pre-filled with the stabilizing agent. Pre-filled syringes, as the term is known in the art, are syringes that are filled by the manufacturer of the filling and shipped to the health care provider ready for use.

A plunger 72 may be situated at open, proximal end 64. Plunger 72 can be moved by means of a plunger rod 74, which is secured to the plunger, for example, by screwing. At the same end where the plunger is situated, the barrel may have a fingergrip 76, which is secured to the barrel according to the so-called snap-cap principle. Fingergrip 76 preferably consists of slightly resilient material, for example plastics. In another embodiment (not shown), the fingergrip is a flange-like part of the barrel projecting radially outwards. Of course, other constructions known to those skilled in the art are possible.

A stopper 78, which closes the barrel, may be situated in the end of the barrel remote from the plunger. The plunger and the stopper are preferably manufactured from an elastic material and, most preferably, from rubber of a pharmaceutical quality.

In the embodiment illustrated, an injection needle 80 is secured to the barrel by means of a needle holder 82. The needle holder has a neck 84, which holds the needle, a shaft 86 and a collar 88. The needle holder is preferably manufactured from slightly resilient material that has resistance to deformation such as, for example, plastics, and is secured to the end of the barrel by means of a snap-cap construction. In the alternative, the needle holder may be secured to the barrel by means of a screwed or adhesive connection or, when the barrel also comprises a collar, by means of a clamping ring. In the latter embodiment, the needle holder may also be flanged around a collar of the barrel.

Although the syringe barrel illustrated in this embodiment includes a locking Luer-type collar 88, it is within the purview of the present invention to include syringe barrels without a collar, syringe barrels having an eccentrically positioned nozzle and various other nozzle-like structures adapted to accept, either permanently or removably, a needle cannula or needle cannula assembly. It is only required that there is an aperture on the distal end of the syringe barrel in fluid communication with the interior of the syringe barrel.

One or more slots 90 may be recessed in the inner wall of shaft 86 and the rear face of neck 84. The slot or slots extend into the rear end of the cannula. In cross-section, the slots may be parts of a circle, but other shapes are also possible, provided the size is such that sufficient injection liquid can be readily passed through; this is achieved if the diameter of the slot or the overall cross-section of the slots is at least as large as that of the cannula. Shaft 86 of needle holder 82 is constructed so that when stopper 78 slides axially forward, it is received, with friction, by the shaft; therefore, apart from slots 90 recessed in the shaft, the inside diameter of the shaft is approximately as large as that of barrel 62. Shaft 86 of needle holder 82 is slightly longer than stopper 78 so that the part 92 of the slot(s) adjoining the barrel is free when the stopper is moved forward against the rear wall of the neck of the needle holder. If desired, needle guard 70 may be constructed to also serve as a plunger rod. In that case, prior to use of the syringe, the needle guard is removed from the needle and secured at the other end of the syringe to the plunger.

Generally, a syringe comprising a needle protector has a safety member, which indicates whether the needle protector has previously been removed. Such a safety member in the form of a cap is described in, for example, U.S. Pat. No. 3,995,630.

Figure 5:
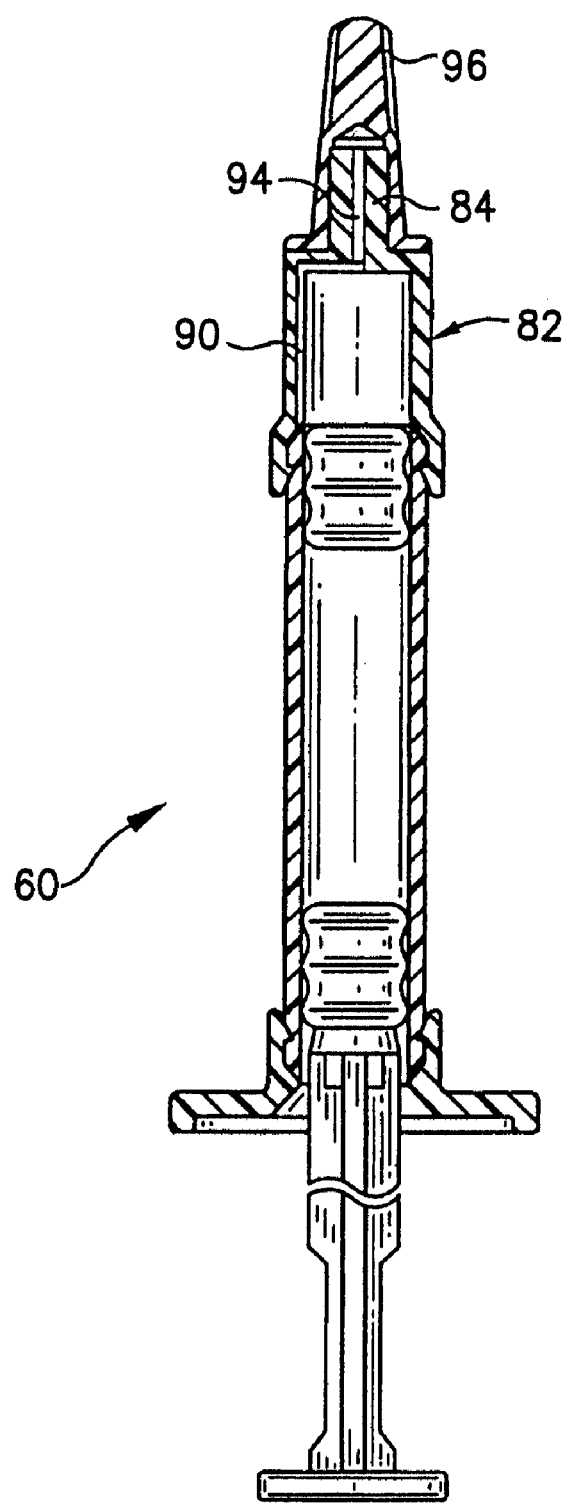
FIG. 5 is a longitudinal sectional view of another embodiment of a syringe.

In further embodiments, the syringe is not stored with a needle in position, i.e., it is a needleless syringe as known in the art. This is illustrated in FIG. 5. With such a syringe, before use, the needle is positioned on neck 84 of needle holder 82 by means of a needle hub. A so-called Luer cone is preferably used for this connection. In this embodiment, aperture 94 in the neck of the needle holder is closed on the outside by a protective cap 96, which ensures the sterility of the syringe as well as the needle holder. Slot 90 recessed in the needle holder projects into the end of the neck aperture.

An example of a suitable syringe is disclosed in U.S. Pat. No. 6,027,481 to Barrelle et al., which is hereby incorporated by reference in its entirety. Other examples of suitable syringes are disclosed in, for example, U.S. Pat. No. 4,964,866 to Szwarc, U.S. Pat. No. 4,986,818 to Imbert et al., U.S. Pat. No. 5,607,400 to Thibault et al. and U.S. Pat. No. 6,263,641 B1 to Odell et al., each of which is hereby incorporated by reference in its entirety.

In a further embodiment, the collection device of the present invention comprises a catheter. As known in the art, catheters are commonly employed when a patient requires repeated doses of medication or other substances. A catheter permits repeated and continuous administration of medication directly into a patient's blood stream, or other region of the body, without repeated injections. Typically, catheters have a hollow tubular lumen, a proximal end and a distal end. The distal end of the catheter, which may be open or closed, is inserted into the vein or artery of a patient.

Figure 6A:
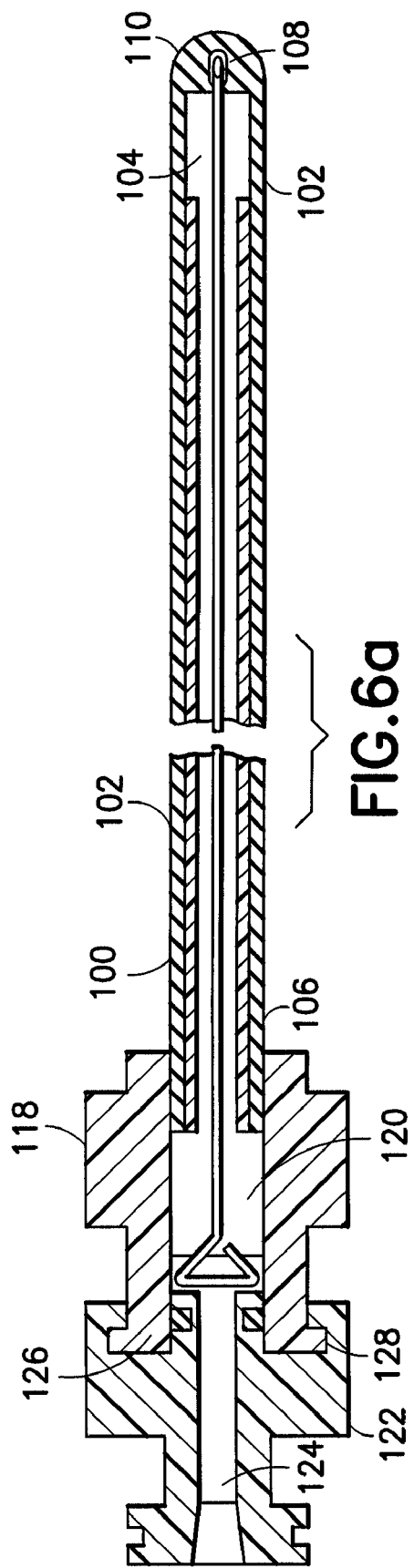
Figure 6B:
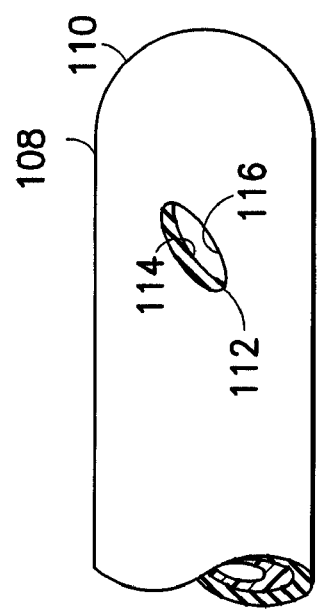
FIG. 6b is a partial side view of the catheter.

FIG. 6a illustrates an exemplary catheter assembly that includes a flexible catheter 100 having a cylindrical side wall 102 describing a lumen 104 therethrough, a proximal end 106 and a closed distal end 108 which, in this illustrated embodiment, has a rounded exterior surface 110 to facilitate insertion of the catheter into the patient. As illustrated in FIG. 6b, catheter 100 includes a slit 112 through side wall 102 adjacent to distal end 108 and is defined by two opposed faces 114 and 116 formed in the side wall. Catheter 100 includes a stabilizing agent according to the present invention, preferably in the lumen of the catheter.

The proximal end of the catheter is connected to a catheter housing 118 having a conduit 120 therethrough. Conduit 120 in the catheter housing and lumen 104 in the catheter are in fluid communication. A valve control knob 122 having a passageway 124 therethrough is rotatably connected to catheter housing 118 so that passageway 124 is in fluid communication with conduit 120. Valve control knob 122 and catheter housing 118 are held together by virtue of proximal flange 126 on the catheter housing which, engages rotational groove 128 in the valve control knob. This structure allows the valve control knob to rotate with respect to the catheter housing but keeps the two elements from coming apart. An example of a suitable catheter is disclosed in U.S. Pat. No. 4,737,152 to Alchas, which is hereby incorporated by reference in its entirety.

In yet a further embodiment, the collection device of the present invention comprises a pipette. In laboratory settings, it is well known to use a pipette to extract a certain volume of a biological fluid from one container and to transport and dispense some or all of the extracted volume into another container. Typically, pipettes are generally hollow tubular members that are used by applying suction at an open upper end, or mouthpiece, in order to extract or aspirate a quantity of fluid medium into the hollow tube. A pressure differential maintained by closing the mouthpiece opening retains the fluid within the pipette allowing transport of the fluid medium to another container. Selective opening of the mouthpiece allows a quantity of the fluid medium contained in the pipette to be dispensed. A certain degree of accuracy in the amount of fluid dispensed is provided by the tapered end portions by reducing the amount of fluid lost due to dripping.

Figure 7:
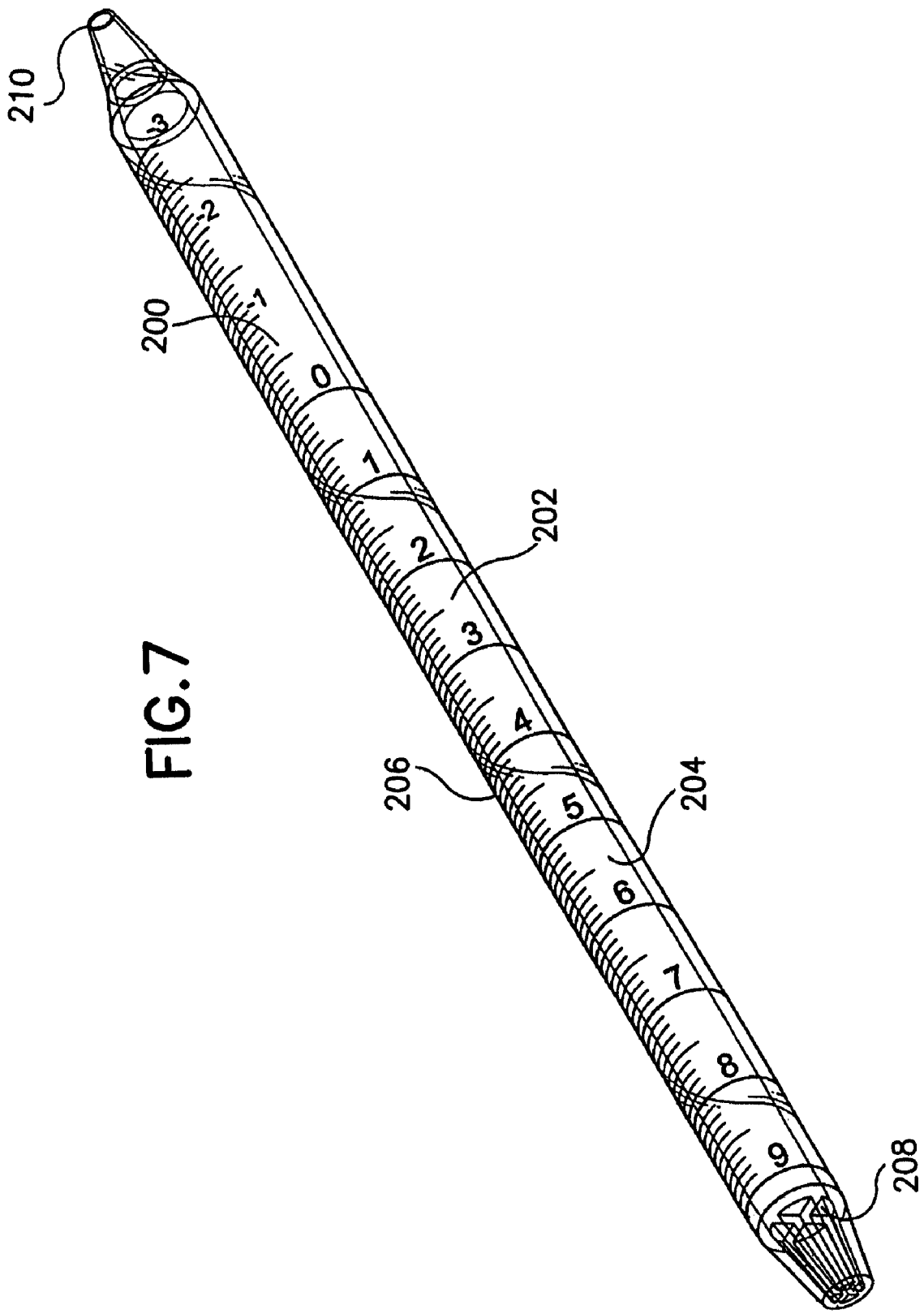
FIG. 7 is a perspective view of a pipette.

Referring now to FIG. 7, an exemplary pipette 200 is shown. Pipette 200 is generally an elongate tubular member defined by a tubular wall 202 of generally uniform thickness. Within tubular wall 202, a pipette interior 204 is defined for accommodating a given volume of fluid medium, for example, a biological sample. Pipette 200 includes an elongate generally cylindrical main body portion 206 that is coextensive with interior 204. Pipette body 206 may be pre-filled with a stabilizing agent according to the present invention.

In order to aspirate and dispense a biological fluid, pipette 200 includes a dispensing portion 208 at one end of body 206 and a mouthpiece 210 at the other end. Both dispensing portion 208 and mouthpiece 210 are in communication with interior 204 of pipette 200 so as to permit aspirating and dispersing of the fluid through dispensing portion 208 by creating a selective pressure differential within interior 204 of pipette 200 using mouthpiece 210. Such a pressure differential can be created manually by opening and closing mouthpiece 210 or may be created by use of mechanical pipette aids.

Pipette 200 may be constructed of glass or a thermoplastic material such as polycarbonate, polyethylene, polyester, polystyrene, polypropylene, polysulfone, polyurethane, ethylene vinyl acetate or the like. Thermoplastic pipettes have largely replaced glass pipettes for many uses. The material of pipette 200 may be transparent, translucent or opaque.

Examples of suitable pipettes are disclosed in, for example, U.S. Pat. No. 6,280,689 B1 to Stevens and U.S. Pat. No. 6,343,717 B1 to Zhang et al., both of which are hereby incorporated by reference in their entirety.

The collection device of the present invention may also comprise a collection bag suitable for holding a biological sample such as, for example, a blood collecting bag, a blood plasma bag, a buffy coat bag, a platelet bag or the like. For ease of description, a blood collecting bag will now be described with reference to FIG. 8.

Figure 8:
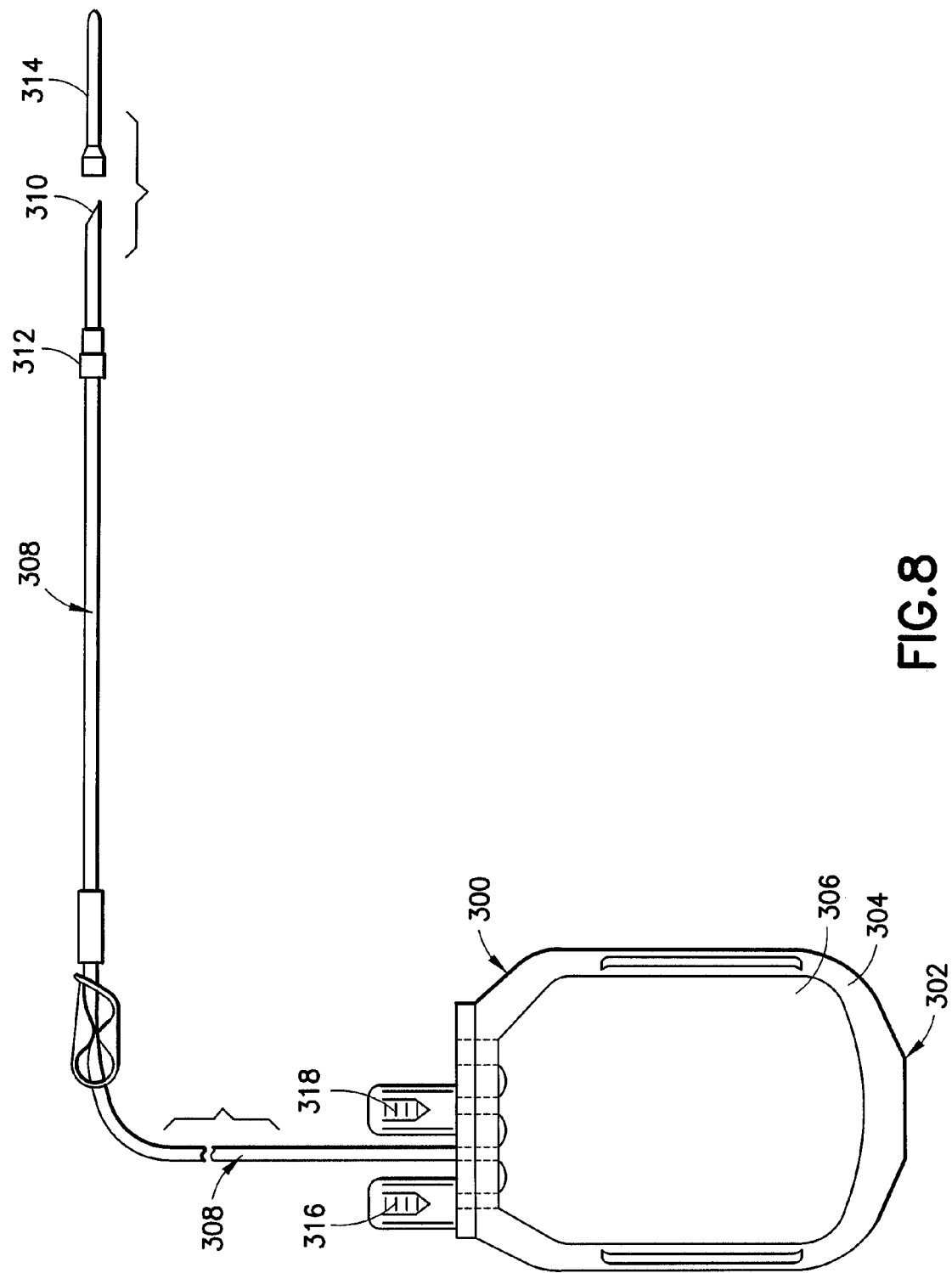
FIG. 8 is a perspective view illustrating a blood collecting bag.

FIG. 8 illustrates a blood collecting bag 300 for accommodating collected blood. Blood collecting bag 300 has a body 302 formed by superposing a pair of identically cut pieces of a sheet material made of a resin, which will be more specifically described hereinafter, and possessed of flexibility and fusing (i.e., heat fusion, high frequency fusion or the like) or adhesively joining to each other the periphery of the sealing portion 304 of each of the pieces of sheet material. A blood-accommodating portion 306 accommodating collected blood is formed at an inner portion surrounded with sealing portion 304 of body 302. Blood collecting bag 300 preferably contains a stabilizing agent in accordance with the present invention.

One end of the flexible tube 308 communicating with blood-accommodating portion 306 is connected with body 302 at an upper portion thereof. A blood collecting needle 310 is installed at the other end of flexible tube 308 through a hub 312. A cap 314, which is to cover blood collecting needle 310, may be installed on hub 312. Two openings 316 and 318, each sealed with a peel tab, may be formed at an upper portion of body 302 such that they can be opened.

The composition, characteristics and the like of the material of the sheets composing body 302 of blood collecting bag 300 are not limited to specified ones. In this case, as the sheet material composing blood collecting bag 300, soft polyvinyl chloride or materials containing the soft polyvinyl chloride as their main component is preferably used. For example, a copolymer containing the soft polyvinyl chloride as its main component and a small amount of macromolecular material, a polymer blend, a polymer alloy and the like can be used. As the plasticizer for the soft polyvinyl chloride, dioctylphthalate (DEHP, di(2-ethylhexyl)phthalate) and (DnDP, di(n-decyl)phthalate) can be preferably used. The content of such a plasticizer in the polyvinyl chloride is preferable to be in the approximate range of 30 to 70 parts by weight, based on 100 parts by weight of polyvinyl chloride.

The other substances that are effectively usable for the sheet material of blood collection bag 300 are polyolefins, i.e., the products of homopolymerization or copolymerization of such olefins or diolefins as ethylene, propylene, butadiene and isoprene. Typical examples include polyethylene, polypropylene, ethylene vinyl acetate copolymer (EVA), polymer blends formed between EVA and various thermoplastic elastomers and arbitrary combinations thereof. Such polyesters as polyethylene terephthalate (PET), polybutylene terephthalate (PBT), poly-1,4-cyclohexane dimethyl terephthalate (PCHT) and polyvinylidene chloride are also usable.

In yet another embodiment, the collection device of the present invention may be a laboratory vessel that contains the stabilizing agent. Particular vessels that can be used in accordance with the present invention include, for example, vials, flasks, spinner flasks, roller bottles, microscope slides, microscope slide assemblies, sample chambers for analytical devices, tapes, laminates, arrays, tubing and the like. Laboratory vessels according to the present invention have at least one operational surface. Many vessels according to the invention have at least one interior wall, which defines a reservoir portion for containing the biological sample, and at least one opening in communication with the reservoir portion.

Plastic or glass is often used to manufacture the laboratory vessels. Some preferred materials used to manufacture laboratory vessels include polypropylene, polyethylene, polyethyleneterephthalate, polystyrene, polycarbonate and cellulosics. Because polypropylene is inexpensive, it is a particularly preferred material for laboratory vessels used for handling and transporting minute and precise amounts of biological sample.

Examples of other suitable materials for the laboratory vessels of the present invention include polyolefins, polyamides, polyesters, silicones, polyurethanes, epoxies, acrylics, polyacrylates, polyesters, polysulfones, polymethacrylates, PEEK, polyimide and fluoropolymers. Glass products including silica glass are also used to manufacture laboratory vessels.

EXAMPLES

Collection systems were made in accordance with the present invention using the following equipment: (1) a spray coater, (2) a dryer, (3) a lyophilizer, (4) a one-up dispenser (or pipetter) for dispensing the stabilizing agent in solution, and (5) a heat sealer for sealing barrier pouches.

Example 1

Plastic Tubes with Mechanical Separator

Fifteen hundred (1,500) plastic tubes were spray coated with a lithium heparin solution and dried. A stabilizing agent was prepared by dissolving SIGMA® protease inhibitor cocktail in deionized water using about 22 ml of deionized water per vial of protease inhibitor. Into each tube was placed approximately 300 μl of the stabilizing agent solution. A mechanical separator was assembled into the closures (HEMOGUARD® closures lubricated with silicone) of each tube and then the closure/separator assemblies were placed on the tubes. Next, the tubes were lyophilized and evacuated. The tubes were then placed into barrier packages, about five (5) tubes per pouch, with desiccant. The pouches were heat sealed, and the product was sterilized.

Example 2

Glass Tubes with Mechanical Separator

The procedure of Example 1 was followed, this time using glass tubes.

Example 3

Plastic Tubes with Mechanical Separator

The procedure of Example 1 is again followed, except that the stabilizing agent solution also includes about 0.5 to about 20% trehalose.

A suitable example of a formulation for a protease inhibitor cocktail is as follows: about 800 μg/ml benzamidine HCL, about 500 μg/ml phenanthroline, about 500 μg/ml aprotinin, about 500 μg/ml leupeptin, about 500 μg/ml pepstatin A and about 50 μg/ml PMSF. The cocktail is in the form of a lyophilized powder. Before use, about 1 ml of pure ethanol is added to the lyophilized powder to obtain a 50× protease inhibitor cocktail.

While various embodiments have been chosen to demonstrate the invention, it will be understood by those skilled in the art that various modifications and additions can be made without departing from the scope of the invention as defined in the appended claims.

What is claimed is:

1. A sterile and evacuated tube for collecting and stabilizing whole blood or a component thereof, comprising a first end and a second end and at least one interior wall defining a reservoir portion for receiving the blood, wherein said reservoir comprises a protein stabilization agent comprising at least two lyophilized protease inhibitors, wherein a first inhibitor is an inhibitor of a serine protease and a second inhibitor is an inhibitor of another class of protease; and a closure pierceable by a needle for supplying blood to said reservoir.

2. The tube of claim 1, wherein said interior wall comprises plastic or glass.

3. The tube of claim 1, wherein said reservoir comprises more than two lyophilized protease inhibitors.

4. The tube of claim 1, wherein said lyophilized protease inhibitors comprise at least two inhibitors of a serine protease and at least one inhibitor of a cysteine protease.

5. The tube of claim 4, wherein said inhibitor of a serine protease is selected from the group consisting of AEBSF, aprotinin, antithrombin, elastatinal, leupeptin, APMSF, DFP and trypsin, and mixtures thereof.

6. The tube of claim 4, wherein said inhibitor of a serine protease comprises AEBSF, aprotinin and leupeptin.

7. The tube of claim 4, wherein said inhibitor of a cysteine protease is E-64.

8. The tube of claim 1, wherein said lyophilized protease inhibitors comprise at least one inhibitor of a serine protease, at least one inhibitor of a cysteine protease, and an inhibitor of a cysteine/serine protease.

9. The tube of claim 8, wherein said inhibitor of a cysteine/serine protease is selected from the group consisting of leupeptin, TPCK, TLCK-HCl (L-1-chloro-3-[4-tosylamidol-7-amino-2-heptanone-HCl), and antipain-HCl, and mixtures thereof.

10. The tube of claim 1, wherein said lyophilized protease inhibitors comprise at least one inhibitor of a serine protease, at least one inhibitor of a cysteine protease, and at least one of an inhibitor of a cysteine/serine protease, an inhibitor of an aspartic protease, an inhibitor of a metalloprotease, and an inhibitor of an exopeptidase.

11. The tube of claim 10, wherein said inhibitor of an aspartic protease is selected from the group consisting of calpain, N-acetyl-leu-leu-norleucinal, N-acetyl-leu-leu-methioninal, pepstatin and VdLPFFVdL, and mixtures thereof.

12. The tube of claim 10, wherein said inhibitor of a metalloprotease is selected from the group consisting of EDTA, 1,10-phenanthroline, phosphoramodon and mixtures thereof.

13. The tube of claim 10, wherein said inhibitor of an exopeptidase is selected from the group consisting of amastatin, bestatin, diprotin A and diprotin B, and mixtures thereof.

14. The tube of claim 1, wherein said at least two lyophilized protease inhibitors comprise AEBSF in a concentration of less than 1 mM at whole blood volume of the collected blood or component thereof.

15. The tube of claim 1, further comprising an anticoagulant.

16. The tube of claim 15, wherein said anticoagulant is spray-dried onto at least, a portion of said interior wall of said tube.

17. The tube of claim 15, wherein said anticoagulant comprises EDTA or a salt thereof.

18. The tube of claim 15, wherein said anticoagulant comprises heparin.

19. The tube of claim 1, further comprising collected blood.

20. The tube of claim 1, further comprising a component of whole blood.

21. The tube of claim 20, wherein said component of whole blood comprises serum or plasma.

22. A kit for collecting and storing a biological sample, comprising: a primary sterile and evacuated collection tube, wherein said primary tube contains a first protein stabilization agent comprising at least two lyophilized protease inhibitors, wherein a first inhibitor is an inhibitor of a serine protease and a second inhibitor is an inhibitor of another class of protease, and a closure pierceable by a needle; and a secondary tube, wherein said secondary tube contains a second protein stabilizing agent.

23. The kit of claim 22, further comprising a tube-to-tube transfer device.

24. The kit of claim 23, wherein said second tube is maintained at a pressure to draw a sample from said first tube through said tube-to-tube transfer device and into said second tube.

25. The kit of claim 22, wherein said secondary tube is sterile.

26. The kit of claim 22, wherein said secondary tube is evacuated.

* * * * *